United States Patent [19]
Carroll et al.

[11] Patent Number: 4,964,406
[45] Date of Patent: Oct. 23, 1990

[54] IMPLANTABLE CARDIAC DEFIBRILLATOR EMPLOYING A SWITCHED CAPACITOR STAGE HAVING A NON-50/50 DUTY CYCLE

[75] Inventors: Kenneth J. Carroll, San Jose; Benjamin D. Pless, Menlo Park, both of Calif.

[73] Assignee: Ventritex, Inc., Sunnyvale, Calif.

[21] Appl. No.: 354,467

[22] Filed: May 19, 1989

[51] Int. Cl.⁵ .............................................. A61N 1/39
[52] U.S. Cl. .................... 128/419 D; 128/419 PG; 128/419 P
[58] Field of Search ......... 128/419 D, 419 PG, 419 P

[56] References Cited

U.S. PATENT DOCUMENTS

| | | | |
|---|---|---|---|
| 4,596,252 | 6/1986 | Nelson | 128/419 PG |
| 4,726,379 | 2/1988 | Altman et al. | 128/419 PG |
| 4,779,618 | 10/1988 | Mund et al. | 128/419 PG |
| 4,790,318 | 12/1988 | Elmqvist et al. | 128/419 PG |
| 4,811,738 | 3/1989 | Economides et al. | 128/419 PG |

OTHER PUBLICATIONS

Brodersen et al., "MOS Switched-Capacitor Filters", *Proceedings of the IEEE*, vol. 67, No. 1, Jan. 1979, pp. 61–75.

*Primary Examiner*—Lee S. Cohen
*Assistant Examiner*—Kennedy J. Schaetzle
*Attorney, Agent, or Firm*—Gerstman & Ellis

[57] ABSTRACT

An implantable cardiac defibrillator employing a switched capacitor stage wherein the switches are clocked in a non-50%/50% ratio such that an operational amplifier has greater than 50% of the clock period to acquire the desired voltage and less than 50% of the clock period to hold the acquired voltage, thereby allowing the circuit to run at an overall lower current drain.

8 Claims, 3 Drawing Sheets

IMPLANTABLE CARDIAC DEFIBRILLATOR EMPLOYING A SWITCHED CAPACITOR STAGE HAVING A NON-50/50 DUTY CYCLE

BACKGROUND OF THE INVENTION

This invention relates generally to implantable medical devices and more particularly, it relates to an implantable cardiac difibrillator employing a switched capacitor stage having a non-50/50 duty cycle for providing a more efficient and effective manner of operating an operational amplifier. In particular, the present invention is directed to an implantable cardiac defibrillator device which utilizes the switched capacitor stage for processing heart signals from the atrium and/or ventricle.

In general, the basis of switched-capacitor circuits is the utilization of a switch-and-capacitor configuration wherein the switch is toggled at a suitably high rate so that the circuit can be made to effectively simulate a resistance. For an understanding of the operation of switched-capacitor circuits and for the purposes of completeness, reference is made to an article entitled "MOS Switched Capacitor Filters" by R. W. Broderson, P. R. Gray and David A. Hodges in *PROC IEEE*, Vol. 67 No. 1, Jan. 1979, pp. 61–75.

As practiced in the prior art, a pair of switches are controlled by two clock generators having the same duty cycle of operation but generating non-overlapping control pulses. A graphic representation of the control pulses PH1 and PH2 used to control respective switches are illustrated in FIGS. 1(a) and 1(b). It will be noted that the clock pulses PH1 and PH2 are high for essentially one-half of each cycle and are low for the other part of the cycle. Thus, the clock pulses are operating with a 50 percent duty cycle minus the non-overlapping period.

With reference to the switched capacitor circuit of FIG. 3, it will be assumed that the switches 22, 28, 36 and 42 are driven by the prior art control pulses PH1 (FIG. 1a) and the switches 26, 30, 34 and 40 are driven by the control pulses PH2 (FIG. 1b). It should be apparent that in the acquisition phase when the pulses PH1 are at a high level, the amplifier 12 is driving the capacitors $C_{LP}$ and $C_F$ as well as any capacitance due to other circuits coupled to the output terminal 18. This results in the need for a relatively large supply of current from the operational amplifier 12. However, in the hold phase when the pulses PH2 are at the high level very little current is demanded of the amplifier since it merely has to counteract the effects of leakage on the output terminal 18.

It has been discovered that by operating the switches in the switched capacitor circuits so as to be closed more than 50 percent of the time during the charge portion of the cycle, the operational amplifier could be operated in a more efficient manner since a small bias current could be used. This provides a longer charge cycle which permits a sufficient time for the voltage on the output terminal of the operational amplifier to reach a stable level with a smaller current drain. Consequently, the bias current of the operational amplifier could be maintained constantly at a relatively low level, thereby reducing power consumption.

SUMMARY OF THE INVENTION

Accordingly, it is a general object of the present invention to provide an implantable medical device employing a switched capacitor stage having a relatively low bias current level in the operational amplifier and thus a reduced power consumption.

It is an object of the present invention to provide an implantable medical device employing a switched capacitor stage wherein switches in the switched capacitor resistor equivalents are operated by clock pulses having a charge portion of more than 50 percent of the cycle time and a discharge portion of less than 50 percent.

In accordance with these aims and objectives, the present invention is concerned with the provision of an implantable cardiac defibrillator employing a switched capacitor stage wherein the switches are clocked in a non-50%/50% ratio such that an operational amplifier has greater than 50% of the clock period to acquire the desired voltage when the current demand is high and less than 50% of the clock period to hold the acquired voltage when the current is carried solely by the switches.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein.

DESCRIPTION OF THE PREFERRED EMBODIMENT

Figure 2:
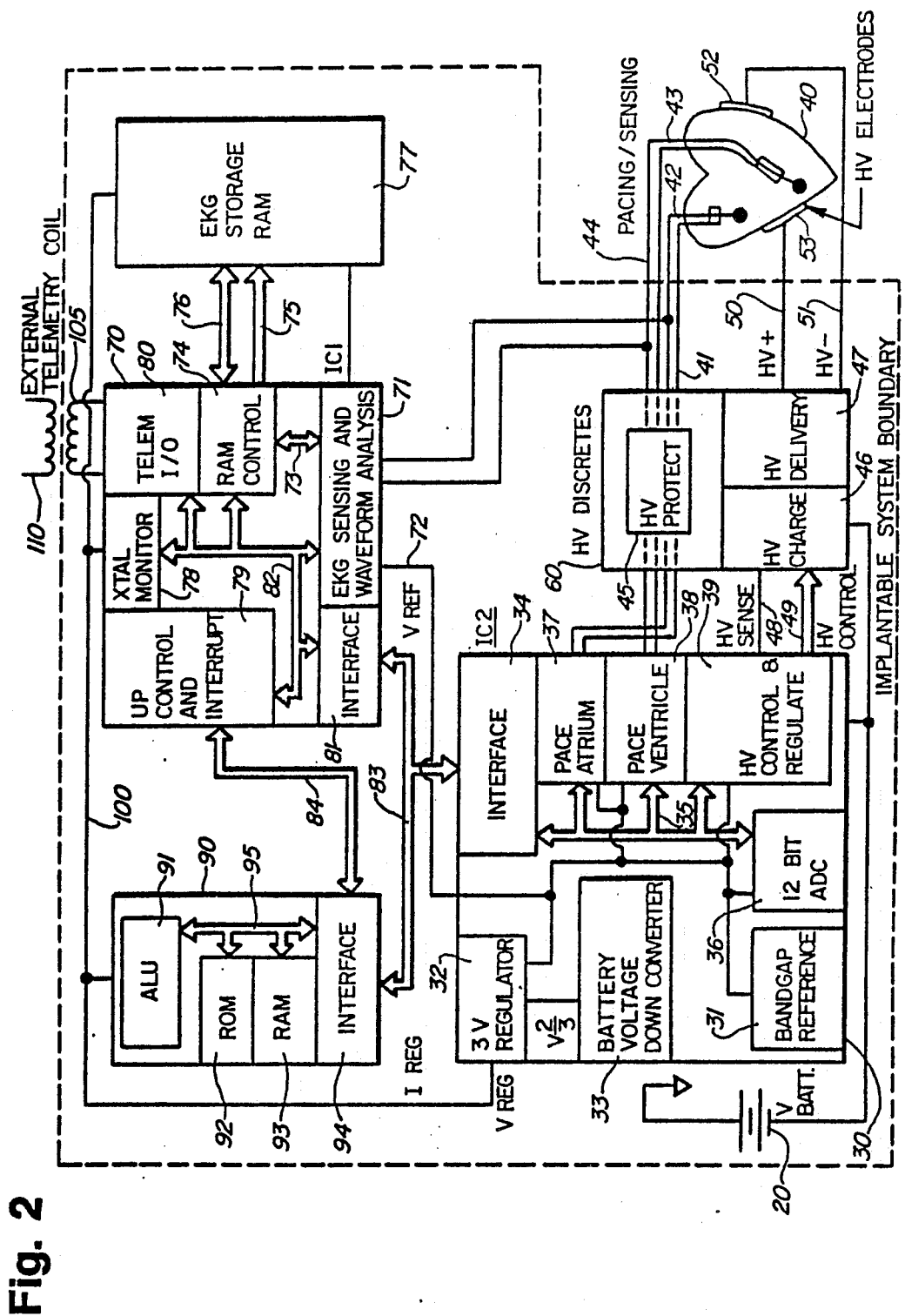
FIG. 2 is a block diagram of an implantable cardiac defibrillator, constructed in accordance with the principles of the present invention.

In FIG. 2, there is illustrated in a functional block diagram format the internal and external elements of an implantable cardiac defibrillator constructed in accordance with the principles of the present invention. A detailed description of the elements of FIG. 2 as well as their interconnection and operation has been presented in co-pending application Ser. No. 344,011, now U.S. Pat. No. 4,949,719 issued Aug. 21, 1990, entitled "Method For Cardiac Defibrillation" and assigned to the same assignee as the present invention, which is hereby incorporated by reference. Thus, the detailed description will not herein be repeated. However, a general description of the elements of FIG. 2 required for an understanding of the present invention will be presented.

In particular, FIG. 2 shows an implantable cardiac defibrillator which includes four integrated circuit chips IC1–IC4 and a set of high voltage discrete component blocks 45–47. The block 45 contains high voltage protection circuits which prevent the atrium and ventricle pacing circuits 37 and 38 from being damaged by the defibrillation voltage. The block 46 is a high voltage charge block and contains a high voltage capacitor that is charged to deliver a defibrillating pulse. The defibrillating pulse is delivered from the high voltage delivery block 47 to electrodes 52 and 53 connected to the heart 40 via lines 50 and 51.

The chip IC1 contains an ECG sensing and waveform analysis block 71 which receives ECG heart signals to be monitored and processed. Specifically, the heart signals coming from the atrium are fed to the sensing and waveform analysis block 71 via the line 42. The heart signals coming from the ventricle are fed to the block 71 via the line 44.

The block 71 includes a first three-stage amplifier/filter network for sensing the heart signals in the atrium and a second three-stage amplifier/filter network for sensing the heart signals in the ventricle. A switched capacitor stage 10 utilized in the first network or second network is illustrated in detail in FIG. 3.

Figure 1:
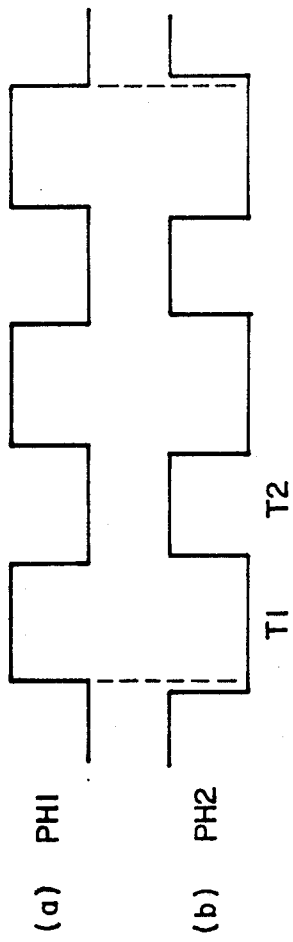
FIGS. 1(a) and 1(b) are graphic representations of the two clock pulses of the prior art.
Figure 3:
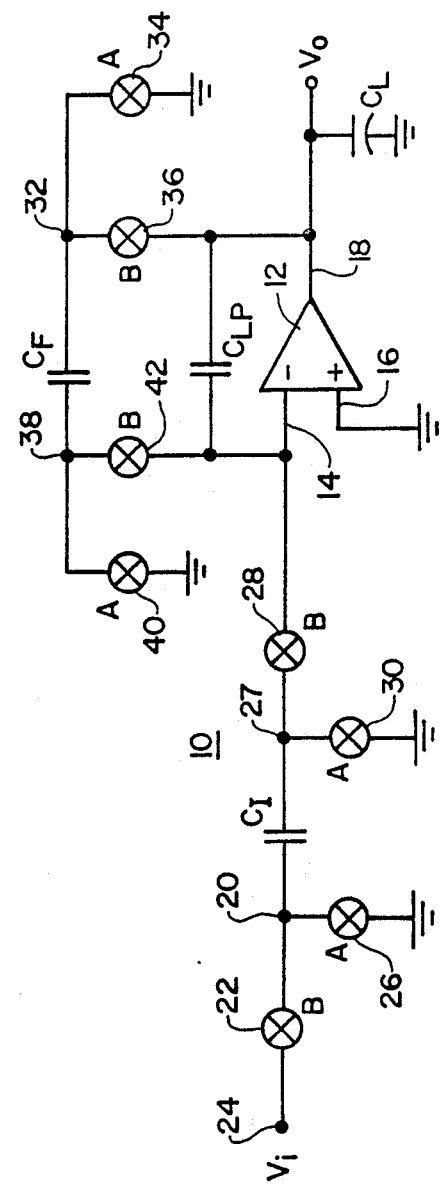
FIG. 3 is a schematic circuit diagram of a switched capacitor stage, constructed in accordance with the principles of the present invention.

Referring now in detail to FIG. 3 of the drawings, there is illustrated in a schematic circuit diagram of a switched capacitor stage 10 constructed in accordance with the principles of the present invention. The switched capacitor stage 10 comprises an operational amplifier 12 which has an inverting input terminal 14, a non-inverting input terminal 16, and an output terminal 18. The non-inverting input terminal 16 is tied to a reference voltage VREF or a ground potential.

An input capacitor $C_I$ has its one end connected to a node 20 and is coupled via a transmission gate 22 to a signal input terminal 24 for receiving an input signal $V_{in}$. The node 20 is also connected to the ground potential by means of a transmission gate 26. The other end of the input capacitor $C_I$ is connected to a node 27 and is coupled via a transmission gate 28 to the inverting input terminal 14 of the operational amplifier. The node 27 is also connected to the ground potential by means of a transmission gate 30. The capacitor $C_I$ together with the transmission gates 22, 26, 28 and 30 function to provide a first switched capacitor resistor equivalent serving as an input resistor.

A feedback resistor $C_F$ has its one end connected to a node 32 and is coupled to the ground potential by means of a transmission gate 34. The node 32 is also coupled to the output terminal 18 of the operational amplifier by means of a transmission gate 36. The other end of the capacitor $C_F$ is connected to a node 38 and is coupled to the ground potential by means of a transmission gate 40. The node 38 is also coupled to the inverting input terminal 14 of the operational amplifier by means of a transmission gate 42. The capacitor $C_F$ together with the transmission gates 34, 36, 40 and 42 function to provide a second switched capacitor resistor equivalent serving as a feedback resistor.

A filter capacitor $C_{LP}$ has its one end connected to the output terminal 18 of the operational amplifier. The other end of the filter capacitor $C_{LP}$ is connected to the inverting input terminal 14 of the operational amplifier. The capacitor $C_{LP}$ serves as a "hold" capacitor as will be explained more fully hereinafter.

Figure 4:
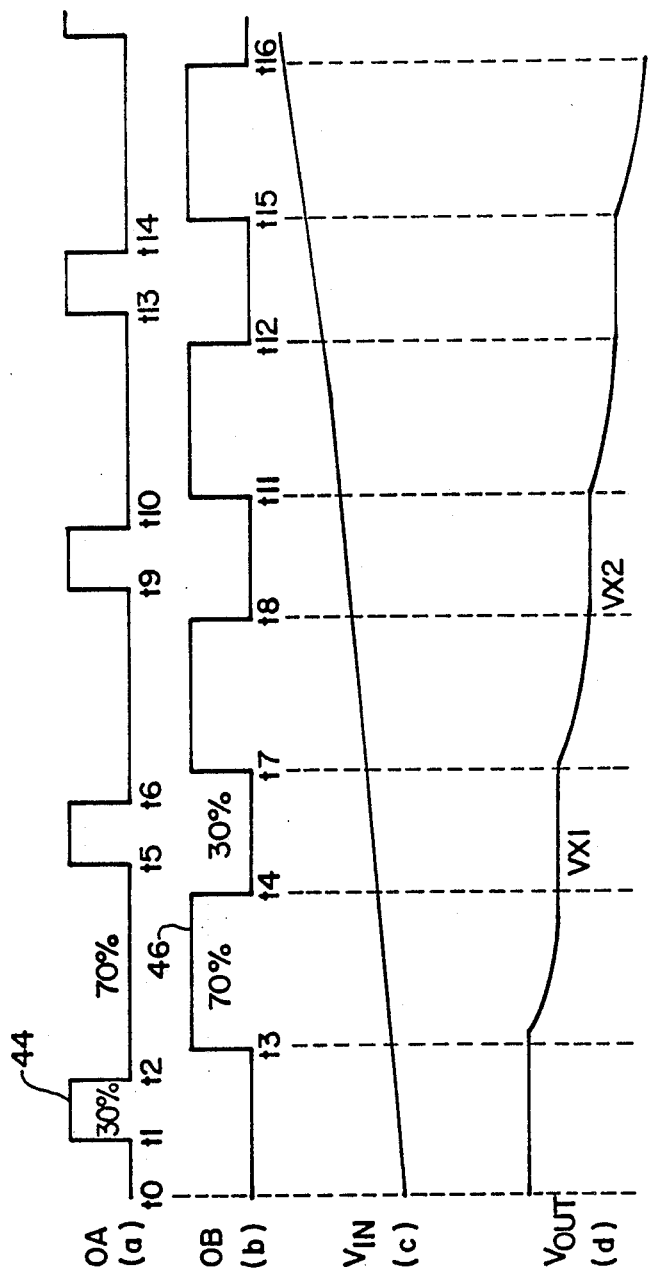
FIGS. 4(a)–4(d) are waveform diagrams useful in understanding the operation of FIG. 3.

FIG. 4(a) illustrates a waveform 44 which represents the pulses of a control signal $\phi A$ that is applied to the control terminals (not shown) of the respective transmission gates 26, 30, 34 and 40. FIG. 4(b) shows a waveform 46 which represents the pulses of a control signal $\phi B$ that is applied to the control terminals (not shown) of the respective transmission gates 22, 28, 36 and 42. While the control signal $\phi B$ has the same frequency, it is delayed in such a manner that the control signals $\phi A$ and $\phi B$ are non-overlapping and operate in what is known as a "break-before-make" fashion. When the control signal $\phi A$ is active or at the logic "1" level such as between the times t1 and t2, this is generally referred to as the "hold" phase. When the control signal $\phi B$ is active or at the logic "1" level such as between the times t3 and t4, this is generally referred to as the "acquiring" or "sample" phase. Unlike the conventional clock pulses of the prior art used to drive the switches in switched capacitor resistor equivalent circuits, each of the control signals $\phi A$ and $\phi B$ is operated with a non-50/50 duty cycle.

In the preferred embodiment of the present invention, the control signal $\phi A$ has a 30/70 percent duty cycle such that the "hold" phase equals 30 percent, and the control signal $\phi B$ has a 70/30 percent duty cycle such that the "sample" phase equals 70 percent. Therefore, during the "hold" phase the control signal $\phi A$ is at a high logic level and the control signal $\phi B$ is at a low logic level. As a result, the transmission gates 26, 30, 34 and 40 are defined to be closed or turned on, and the transmission gates 22, 28, 36 and 42 are defined to be opened or turned off.

On the other hand, during the "sample" phase the control signal $\phi B$ is at the high logic level and the control signal $\phi A$ is at the low logic level. Consequently, the transmission gates 22, 28, 36 and 42 are defined to be closed or turned on, and the transmission gates 26, 30, 34 and 40 are defined to be opened or turned off.

The operation of the switched capacitor stage 10 will now be explained with reference to the waveform diagrams of FIGS. 4(a) through 4(d). Initially, it will be assumed that prior to the time $t\phi$ all of the capacitors $C_I$, $C_F$ and $C_{LP}$ have been completely discharged. A ramp input signal $V_{in}$ is applied to the signal input terminal 24 at the time $t\phi$, as illustrated in FIG. 4(c). At the time t1, the control signal $\phi A$ makes a low-to-high transition and the control signal $\phi B$ remains at the low logic level. During the "hold" phase between the times t1 and t2, the transmission gates 26, 30, 34 and 40 are closed so as to discharge the capacitors $C_I$ and $C_F$, and the transmission gates 22, 28, 36 and 42 are opened. Thus, the operational amplifier 12 is required to supply very little current during this "hold" phase because the load capacitance and $C_{LP}$ have been precharged during the acquiring phase, therefore the amplifier merely has to counteract the effects of leakage on node 18.

The "hold" capacitor $C_{LP}$ will hold the charge between the times t1 and t2. Further, since there was assumed that this capacitor was discharged initially, terminal 18 will be at zero volts, as illustrated in FIG. 4(d). At the time t2, the control signal $\phi A$ will make a high-to-low transition so as to turn off the transmission gates 26, 30, 34 and 40. Then, after a short delay the control signal $\phi B$ will make a low-to-high transition at the time t3. The control signals $\phi A$ and $\phi B$ are illustrated in respective FIGS. 4(a) and 4(b).

During the "sample" phase between the times t3 and t4, the transmission gates 26, 30, 34 and 40 are opened, and the transmission gates 22, 28, 36 and 42 are closed so as to permit the initial charging of the capacitor $C_I$, to the applied input voltage $V_{in}$ and $C_{LP}$ and $C_F$ to the output voltage $V_{out}$. Consequently, the operational amplifier is required to drive a high capacitive load of $C_F$, $C_{LP}$ and the load $C_L$ and thus needs a high bias current. It has been discovered that by making the charging or sampling time longer, this allows the operational amplifier to drive the output voltage $-V_{out}$ on the output terminal 18 to a stable level with a smaller bias current level. As a result, the operational amplifier is operated on a more efficient and effective manner than those of the prior art, thereby reducing overall power consumption.

During the time t3 to the time t4, the output voltage, $V_{out}$, will reduce due to the charging of the capacitors $C_I$, $C_F$ and $C_{LP}$. At the time t4, the control signal $\phi B$ will make a high-to-low transition causing the transmission gates 22, 28, 36 and 42 to open and thus to discontinue the charging process. However, the voltage $V_{x1}$ on the capacitor $C_{LP}$ will be held between the times t4 and t7. Again, during the times between t5 and t6, the transmission gates 26, 30, 34 and 40 will be closed, thereby permitting the discharge of the input capacitor $C_I$ and the feedback capacitor $C_F$. This process is repeated over and over again.

Referring now to FIG. 4(d), the output voltage, $V_{out}$, will charge to the voltage of $V_{x2}$ between the times t7 and t8 and will be held at this level between the next "hold" phase (from times t9 to t10). As can be seen, the output voltage is a discrete time, inverted and gained up version of the input voltage $V_{in}$. With the transmission gates of the first and second switched capacitor resistor equivalent operating with a 70/30 percent duty cycle where the "sample" phase is 70 percent and the "hold" phase is 30 percent, the output voltage $V_{out}$ will appear as illustrated in FIG. 4(d).

From the foregoing detailed description, it can thus be seen that the present invention provides an implantable cardiac defibrillator employing a switched capacitor stage which includes an operational amplifier, a first switched capacitor resistor serving as an input resistor, and a second switched capacitor resistor serving as a feedback resistor. The switches in the first and second switched capacitor resistors are operated by control signals having a non-50/50 duty cycle. As a result, the operational amplifier can be operated with a relatively low bias current.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. An implantable medical device comprising:
   electrode means adapted for coupling to a patient's heart;
   sensing means having inputs connected to said electrode means for sensing cardiac electrical signals;
   said sensing means including switched capacitor means having switches clocked by first and second control signals with a non-50/50 percent duty cycle;
   said switched capacitor means comprising operational amplifier means having an inverting input terminal, a non-inverting input terminal and an output terminal;
   said operational amplifier means having greater than 50 percent of the clock period to acquire a desired voltage on the output terminal and less than 50 percent of the clock period to hold the acquired voltage.

2. An implantable medical device as claimed in claim 1, wherein said first control signal has approximately a 30/70 percent duty cycle and said second control signal has approximately a 70/30 percent duty cycle.

3. An implantable medical device as claimed in claim 1, wherein said first control signal is at a high logic level for less than 50 percent of the clock period and said second control signal is at a high logic level greater than 50 percent of the clock period.

4. An implantable medical device comprising:
   electrode means adapted for coupling to a patient's heart;
   sensing means having inputs connected to said electrode means for sensing cardiac electrical signals;
   means for storing a charge;
   means for discharging said storage means to shock the heart via the electrode means;
   said sensing means including switched capacitor means formed of operational amplifier means and switch means, said switch means being clocked by first and second control signals with a non-50/50 percent duty cycle;
   said operational amplifier means having greater than 50 percent of the clock period to acquire a desired voltage and less than 50 percent of the clock period to hold the acquired voltage.

5. An implantable medical device as claimed in claim 4, wherein said first control signal has approximately a 30/70 percent duty cycle and said second control signal has approximately a 70/30 percent duty cycle.

6. An implantable medical device as claimed in claim 4, wherein said first control signal is at a high logic level for less than 50 percent of the clock period and said second control signal is at a high logic level greater than 50 percent of the clock period.

7. An implantable medical device comprising:
   electrode means adapted for coupling to a patient's heart;
   sensing means having inputs connected to said electrode means for sensing cardiac electrical signals;
   said sensing means including switched capacitor means having switches clocked by first and second control signals with a non-50/50 percent duty cycle; and
   said first control signal having approximately a 30/70 percent duty cycle and said second control signal has approximately a 70/30 percent duty cycle.

8. An implantable medical device comprising:
   electrode means adapted for coupling to a patient's heart;
   sensing means having inputs connected to said electrode means for sensing cardiac electrical signals;
   means for storing a charge;
   means for discharging said storage means to shock the heart;
   said sensing means including switched capacitor means formed of operational amplifier means and switch means, said switch means being clocked by first and second control signals with a non-50/50 percent duty cycle;
   said first control signal having approximately a 30/70 percent duty cycle and said second control signal has approximately a 70/30 percent duty cycle.

* * * * *